(12) United States Patent
Kalbe et al.

(10) Patent No.: US 7,914,816 B2
(45) Date of Patent: Mar. 29, 2011

(54) ENDOPARASITICIDAL AGENTS FOR VOLUNTARY ORAL INGESTION BY ANIMALS

(75) Inventors: Jochen Kalbe, Leichlingen (DE); Kornelia Geißler, Köln (DE); Michael Träubel, Köln (DE); Achim Harder, Köln (DE); Georg von Samson-Himmelstjerna, Mellendorf (DE)

(73) Assignee: Bayer Animal Health GmbH (DE)

( * ) Notice: Subject to any disclaimer, the term of this patent is extended or adjusted under 35 U.S.C. 154(b) by 836 days.

(21) Appl. No.: 10/311,419

(22) PCT Filed: Jun. 18, 2001

(86) PCT No.: PCT/EP01/06836
§ 371 (c)(1),
(2), (4) Date: Sep. 26, 2003

(87) PCT Pub. No.: WO02/00202
PCT Pub. Date: Jun. 3, 2002

(65) Prior Publication Data
US 2004/0043925 A1 Mar. 4, 2004

(30) Foreign Application Priority Data
Jun. 26, 2000 (DE) .................................. 100 31 044

(51) Int. Cl.
*A61K 9/48* (2006.01)
*A61K 9/20* (2006.01)
(52) U.S. Cl. ........................................ 424/451; 424/464
(58) Field of Classification Search .................. None
See application file for complete search history.

(56) References Cited

U.S. PATENT DOCUMENTS

| | | | |
|---|---|---|---|
| 3,137,592 A | 6/1964 | Protzman et al. | |
| 3,899,607 A * | 8/1975 | Miller et al. | 426/285 |
| 4,678,516 A | 7/1987 | Alderman et al. | |
| 4,851,226 A | 7/1989 | Julian et al. | |
| 4,857,333 A | 8/1989 | Harold | |
| 4,948,615 A | 8/1990 | Zallie et al. | |
| 5,116,815 A | 5/1992 | Takagi et al. | |
| 5,405,564 A | 4/1995 | Stepto et al. | |
| 5,411,735 A | 5/1995 | Daoudal | |
| 5,456,923 A | 10/1995 | Nakamichi et al. | |
| 5,514,773 A | 5/1996 | Nishiyama et al. | |
| 5,646,244 A | 7/1997 | Nishiyama et al. | |
| 5,656,464 A | 8/1997 | Jeschke et al. | |
| 5,663,140 A | 9/1997 | Scherkenbeck et al. | 514/11 |
| 5,695,749 A | 12/1997 | Friess et al. | |
| 5,717,063 A | 2/1998 | Scherkenbeck et al. | |
| 5,747,448 A | 5/1998 | Ohyama et al. | |
| 5,777,075 A | 7/1998 | Scherkenbeck et al. | |
| 5,821,222 A | 10/1998 | Bonse et al. | |
| 5,824,336 A | 10/1998 | Jans et al. | |

(Continued)

FOREIGN PATENT DOCUMENTS

DE 4233625 A1 4/1994

(Continued)

OTHER PUBLICATIONS

PCT International Search Report, Dated Dec. 13, 2001, 6 pages. M. Thomas et al., Physical quality of pelleted animal feed 3. Contribution of feedstuff components, Animal Feed Science and Technology, vol. 70, Issues 1-2, Jan. 1998, pp. 59-78.

*Primary Examiner* — Carlos A Azpuru

(57) ABSTRACT

The present invention relates to pharmaceutical presentations for animals which are administered orally and which are accepted readily by the animals (for example dogs, cats and horses), to processes for their preparation and to their use, in particular as endoparasiticides.

14 Claims, 1 Drawing Sheet

| U.S. PATENT DOCUMENTS | | | | FOREIGN PATENT DOCUMENTS | | |
|---|---|---|---|---|---|---|
| 5,856,436 A | 1/1999 | Nishiyama et al. | | DE | 19853729 | 7/2006 |
| 5,866,189 A | 2/1999 | Garwood et al. | | EP | 0118240 A2 | 9/1984 |
| 5,874,530 A | 2/1999 | Scherkenbeck et al. | | EP | 0320320 A2 | 6/1989 |
| 6,033,879 A | 3/2000 | Jeschke et al. | | EP | 0390 960 * | 10/1990 |
| 6,051,253 A | 4/2000 | Zettler et al. | | EP | 796565 | 9/1997 |
| 6,063,821 A | 5/2000 | Breitenbach et al. | | FR | 2702960 A1 | 9/1994 |
| 6,149,941 A | 11/2000 | Schwarz et al. | | FR | 2751848 A1 | 2/1998 |
| 6,329,338 B1 | 12/2001 | Sakanaka et al. | | | | |
| 6,387,381 B2 | 5/2002 | Christensen | | * cited by examiner | | |
| 6,497,899 B2 | 12/2002 | Thombre et al. | | | | |

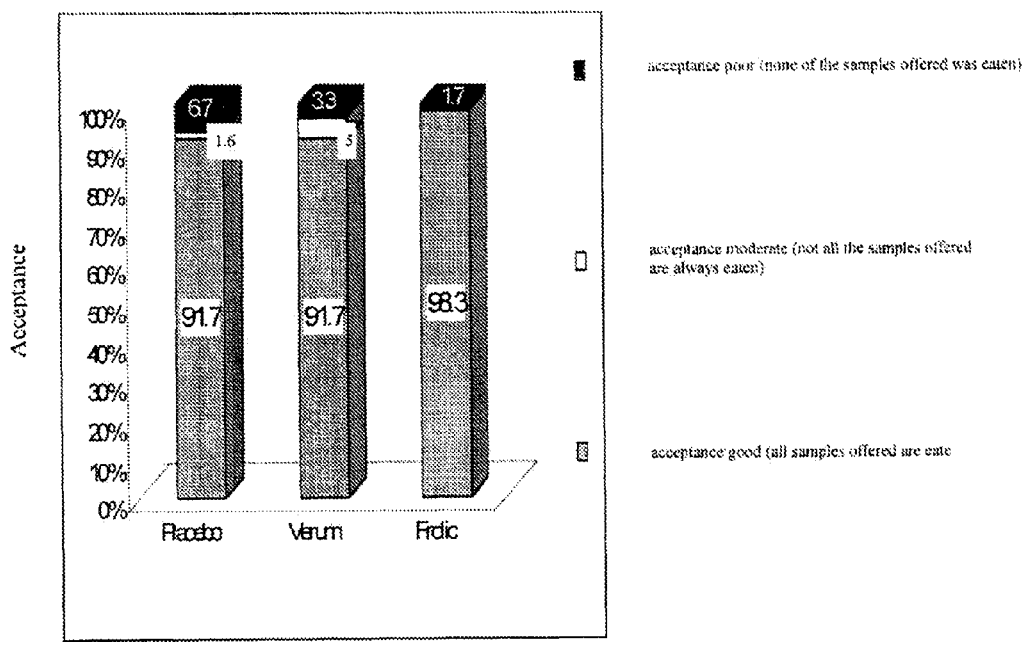
Figure

ENDOPARASITICIDAL AGENTS FOR VOLUNTARY ORAL INGESTION BY ANIMALS

The present invention relates to pharmaceutical presentations for animals which are administered orally and which are accepted readily by the animals (for example dogs, cats and horses).

To administer drugs orally, it is generally customary, also for veterinary purposes, to preferably use tablets, that is to say compressed materials of active compound and ancilliary material. These are quite unattractive for the animals and are, as a rule, only accepted reluctantly so that the animal keeper must wrap the tablets in food in order to administer them. This does not always guarantee that all of the medicament, and thus the correct dose of the medicament, can be administered.

The palatability of these tablets can be increased for example by adding various aromas and flavourings (DEA 196 17 487, WO 95/31963, U.S. Pat. No. 4,851,226). In addition, the shape of the tablet may be altered, for example into the shape of a bone when used for dogs (U.S. Pat. No. 4,857,333). Furthermore, laminated tablets are prepared which contain attractants as the outer layer (EP A 320 320, EP A 574 301). The main disadvantage of these improved tablet systems is that the animal can clearly distinguish them from normal feed, so that complete acceptance cannot be achieved even with these systems.

The melt extrusion into tablets of suitable polymers for oral administration is known for use in humans, but the acceptance of these tablets by animals is insufficient owing to their consistency (WO 96/29053).

It is known that the extrusion of starch allows a very wide range of shaped articles to be produced which are employed in particular in the feeds industry (U.S. Pat. No. 3,899,607). However, the suitability of these feeds as carriers for pharmaceutical active compounds is only limited since they contain up to 50% meat and thus do not comply with the rules of a pharmaceutical presentation. However, the acceptance of these extrudates is very good, owing to the added meat and the shape.

In contrast, no acceptance was found with pure starch extrudates for pharmaceutical active compounds (EP A 0 118 240, EP A 390 960). The attraction of feed extrudates depends primarily on the flavouring, but also decisively on the physical composition [M. Thomas et al, Animal Feed Science Technology 70 (1998) 59-78].

To make the administration of endoparasiticidal active compounds as simple as possible for the animal keeper, it is therefore desirable to provide a composition which is accepted readily by the animal.

Surprisingly, there have now been found starch-based extruded shaped articles as pharmaceutical presentation which act as carriers for pharmaceutical active compounds and are without added meat, but which are accepted readily by the animals.

Also subject-matter of the present invention is the use of this pharmaceutical presentation as carrier for pharmaceutical active compounds in veterinary medicine, in particular for endoparasiticidally active cyclic depsipeptides, as they are described, for example, in EP-OS 382 173 and DE-A 4 317 432.9; DE-A 4 317 457.4; DE-A 4 317 458.2.

Subject-matter of the present invention are:
1. Starch-based extruded shaped articles, characterized in that they comprise specific aromas, bodying agents and pharmaceutical active compounds for animals.
2. Starch-based extruded shaped articles according to Item 1, characterized in that they contain poultry liver aroma or meat aroma as aromas.
3. Starch-based extruded shaped articles according to Item 1, characterized in that they have a Shore A hardness of 10 to 100.
4. Starch-based extruded shaped articles according to Items 1 and 2, characterized in that they contain cyclic depsipeptides composed of amino acids and hydroxycarboxylic acids as units and having 6 to 30 ring or chain atoms.
5. Starch-based extruded shaped articles according to Items 1, 2 and 3, characterized in that they have added to them pulverulent cellulose acetate.
6. Starch-based extruded shaped articles according to Items 1, 2, 3 and 4, characterized in that they contain further ancilliary materials such as emulsifiers, humectants and preservatives.
7. Process for the preparation of starch-based extruded shaped articles according to Items 1, 2, 3, 4 and 5, characterized in that the starting materials are mixed and processed at temperatures of less than 150° C.

Active compounds which are suitable are, in principle, all active compounds which are suitable for use in veterinary medicine. Especially suitable are the active compounds from the class of the depsipeptides, in particular cyclic depsipeptides.

Preferred cyclic depsipeptides are those having 18 to 24 ring atoms, in particular 24 ring atoms.

The depsipeptides having 18 ring atoms include compounds of the general formula (I):

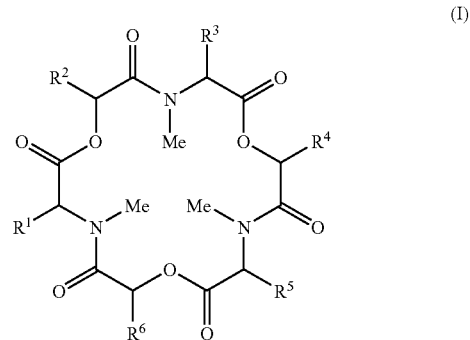

in which
$R^1$, $R^3$ and $R^5$ independently of one another represent hydrogen, straight-chain or branched alkyl having up to 8 carbon atoms, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl which can optionally be substituted by one or two benzyloxycarbonyl radicals or by one, two, three or four alkyl radicals, or represent alkoxycarbonylaminoalkyl, 9-fluorenylmethoxycarbonyl(Fmoc)-aminoalkyl, alkenyl, cycloalkyl, cycloalkylalkyl and optionally substituted arylalkyl, substituents which may be mentioned being halogen, hydroxyl, alkyl and alkoxy,
$R^2$, $R^4$ and $R^6$ independently of one another represent hydrogen, straight-chain or branched alkyl having up to 8 carbon atoms, hydroxyalkyl, mercaptoalkyl, alkanoyloxyalkyl, alkoxyalkyl, aryloxyalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, alkoxycarbonylaminoalkyl, alkenyl, cycloalkyl, cycloalkylalkyl, optionally substituted aryl or arylalkyl, substituents which may be mentioned being halogen, hydroxyl, alkyl, alkyoxy, and their optical isomers and racemates.

Preferred are compounds of the formula (I),

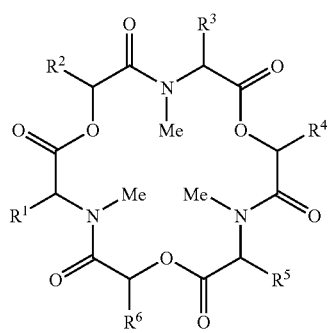

(I)

in which $R^1$, $R^3$ and $R^5$ independently of one another represent straight-chain or branched $C_1$-$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxy-$C_1$-$C_6$-alkyl, in particular hydroxymethyl, 1-hydroxyethyl, $C_1$-$C_4$-alkanoyloxy-$C_1$-$C_6$-alkyl, in particular acetoxymethyl, 1-acetoxyethyl, $C_1$-$C_4$-alkoxy-$C_1$-$C_6$-alkyl, in particular methoxymethyl, 1-methoxyethyl, aryl-$C_1$-$C_4$-alkyloxy-$C_1$-$C_6$-alkyl, in particular benzyloxymethyl, 1-benzyloxyethyl, mercapto-$C_1$-$C_6$-alkyl, in particular mercaptomethyl, $C_1$-$C_4$-alkylthio-$C_1$-$C_6$-alkyl, in particular methylthioethyl, $C_1$-$C_4$-alkylsulphinyl-$C_1$-$C_6$-alkyl, in particular methylsulphinylethyl, $C_1$-$C_4$-alkylsulphonyl-$C_1$-$C_6$-alkyl, in particular methylsulphonylethyl, carboxy-$C_1$-$C_6$-alkyl, in particular carboxymethyl, carboxyethyl, $C_1$-$C_4$-alkoxycarbonyl-$C_1$-$C_6$-alkyl, in particular methoxycarbonylmethyl, ethoxycarbonylethyl, $C_1$-$C_4$-arylalkoxycarbonyl-$C_1$-$C_6$-alkyl, in particular benzyloxycarbonylmethyl, carbamoyl-$C_1$-$C_6$-alkyl, in particular carbamoylmethyl, carbamoylethyl, amino-$C_1$-$C_6$-alkyl, in particular aminopropyl, aminobutyl, $C_1$-$C_4$-alkylamino-$C_1$-$C_6$-alkyl, in particular methylaminopropyl, methylaminobutyl, $C_1$-$C_4$-dialkylamino-$C_1$-$C_6$-alkyl, in particular dimethylaminopropyl, dimethylaminobutyl, guanido-$C_1$-$C_6$-alkyl, in particular guanidopropyl, $C_1$-$C_4$-alkoxycarbonylamino-$C_1$-$C_6$-alkyl, in particular tert-butoxycarbonylaminopropyl, tert-butoxycarbonylaminobutyl, 9-fluorenyl-methoxycarbonyl(Fmoc)amino-$C_1$-$C_6$-alkyl, in particular 9-fluorenyl-methoxy-carbonyl(Fmoc)aminopropyl, 9-fluorenyl-methoxycarbonyl(Fmoc)aminobutyl, $C_2$-$C_8$-alkenyl, in particular vinyl, allyl, butenyl, $C_3$-$C_7$-cycloalkyl, in particular cyclopentyl, cyclohexyl, cycloheptyl, $C_3$-$C_7$-cycloalkyl-$C_1$-$C_4$-alkyl, in particular cyclopentylmethyl, cyclohexylmethyl, cycloheptylmethyl, phenyl-$C_1$-$C_4$-alkyl, in particular phenylmethyl which can optionally be substituted by radicals from the series halogen, in particular fluorine, chlorine, bromine or iodine, hydroxyl, $C_1$-$C_4$-alkoxy, in particular methoxy or ethoxy, and $C_1$-$C_4$-alkyl, in particular methyl, $R^2$, $R^4$ and $R^6$ independently of one another represent straight-chain or branched $C_1$-$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxy-$C_1$-$C_6$-alkyl, in particular hydroxymethyl, 1-hydroxyethyl, $C_1$-$C_4$-alkanoyloxy-$C_1$-$C_6$-alkyl, in particular acetoxymethyl, 1-acetoxyethyl, $C_1$-$C_4$-alkoxy-$C_1$-$C_6$-alkyl, in particular methoxymethyl, 1-methoxyethyl, aryl-$C_1$-$C_4$-alkyloxy-$C_1$-$C_6$-alkyl, in particular benzyloxymethyl, 1-benzyloxyethyl, mercapto-$C_1$-$C_6$-alkyl, in particular mercaptomethyl, $C_1$-$C_4$-alkylthio-$C_1$-$C_6$-alkyl, in particular methylthioethyl, $C_1$-$C_4$-alkylsulphinyl-$C_1$-$C_6$-alkyl, in particular methylsulphinylethyl, $C_1$-$C_4$-alkylsulphonyl-$C_1$-$C_6$-alkyl, in particular methylsulphonylethyl, carboxy-$C_1$-$C_6$-alkyl, in particular carboxymethyl, Carboxyethyl, $C_1$-$C_4$-alkoxycarbonyl-$C_1$-$C_6$-alkyl, in particular methoxycarbonylmethyl, ethoxycarbonylethyl, $C_1$-$C_4$-arylalkoxycarbonyl-$C_1$-$C_6$-alkyl, in particular benzyloxycarbonylmethyl, carbamoyl-$C_1$-$C_6$-alkyl, in particular carbamoylmethyl, carbamoylethyl, amino-$C_1$-$C_6$-alkyl, in particular aminopropyl, aminobutyl, $C_1$-$C_4$-alkylamino-$C_1$-$C_6$-alkyl, in particular methylaminopropyl, methylaminobutyl, $C_1$-$C_4$-dialkylamino-$C_1$-$C_6$-alkyl, in particular dimethylaminopropyl, dimethylaminobutyl, $C_2$-$C_8$-alkenyl, in particular vinyl, allyl, butenyl, $C_3$-$C_7$-cycloalkyl, in particular cyclopentyl, cyclohexyl, cycloheptyl, $C_3$-$C_7$-cycloalkyl-$C_1$-$C_4$-alkyl, in particular cyclopentylmethyl, cyclohexylmethyl, cycloheptylmethyl, phenyl, phenyl-$C_1$-$C_4$-alkyl, in particular phenylmethyl which can optionally be substituted by radicals from the series halogen, in particular fluorine, chlorine bromine or iodine, hydroxyl, $C_1$-$C_4$-alkoxy, in particular methoxy or ethoxy, and $C_1$-$C_4$-alkyl, in particular methyl, and their optical isomers and racemates.

Especially preferred are compounds of the formula (I), in which $R^1$, $R^3$ and $R^5$ independently of one another represent $C_1$-$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, hydroxy-$C_1$-$C_6$-alkyl, in particular hydroxymethyl, 1-hydroxyethyl, $C_1$-$C_4$-alkanoyloxy-$C_1$-$C_6$-alkyl, in particular acetoxymethyl, I-acetoxyethyl, $C_1$-$C_4$-alkoxy-$C_1$-$C_6$-alkyl, in particular methoxymethyl, 1-methoxyethyl, aryl-$C_1$-$C_4$-alkyloxy-$C_1$-$C_6$-alkyl, in particular benzyloxymethyl, 1-benzyloxyethyl, $C_1$-$C_4$-alkoxycarbonylamino-$C_1$-$C_6$-alkyl, in particular tert-butoxycarbonylaminopropyl, tert-butoxycarbonylaminobutyl, $C_2$-$C_8$-alkenyl, in particular vinyl, allyl, $C_3$-$C_7$-cycloalkyl, in particular cyclopentyl, cyclohexyl, cycloheptyl, $C_3$-$C_7$-cycloalkyl-$C_1$-$C_4$-alkyl, in particular cyclopentylmethyl, cyclohexylmethyl, cycloheptylmethyl, phenyl-$C_1$-$C_4$-alkyl, in particular phenylmethyl which can optionally be substituted by one or more identical or different radicals from amongst those stated above, $R^2$, $R^4$ and $R^6$ independently of one another represent straight-chain or branched $C_1$-$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxy-$C_1$-$C_6$-alkyl, in particular hydroxymethyl, aryl-$C_1$-$C_4$-alkyloxy-$C_1$-$C_6$-alkyl, in particular benzyloxymethyl, 1-benzyloxyethyl, carboxy-$C_1$-$C_6$-alkyl, in particular carboxymethyl, carboxyethyl, $C_1$-$C_4$-alkoxycarbonyl-$C_1$-$C_6$-alkyl, in particular methoxycarbonylmethyl, ethoxycarbonylethyl, $C_1$-$C_4$-arylalkoxycarbonyl-$C_1$-$C_6$-alkyl, in particular benzyloxycarbonylmethyl, $C_1$-$C_4$-alkylamino-$C_1$-$C_6$-alkyl, in particular methylaminopropyl, methylaminobutyl, $C_1$-$C_4$-dialkylamino-$C_1$-$C_6$-alkyl, in particular dimethylaminopropyl, dimethylaminobutyl, $C_2$-$C_6$-alkenyl, in particular vinyl, allyl, butenyl, $C_3$-$C_7$-cycloalkyl, in particular cyclopentyl, cyclohexyl, cycloheptyl, $C_3$-$C_7$-cycloalkyl-$C_1$-$C_4$-alkyl, in particular cyclopentylmethyl, cyclohexylmethyl, cycloheptylmethyl, phenyl, phenyl-$C_1$-$C_4$-alkyl, in particular phenylmethyl which can optionally be substituted by one or more identical or different radicals from amongst those stated above, and their optical isomers and racemates.

Very especially preferred are compounds of the formula (I),
in which
$R^1$, $R^3$ and $R^5$ independently of one another represent straight-chain or branched $C_1$-$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, $C_2$-$C_8$-alkenyl, in particular allyl, $C_3$-$C_7$-cycloalkyl-$C_1$-$C_4$-alkyl, in particular cyclohexylmethyl, phenyl-$C_1$-$C_4$-alkyl, in particular phenylmethyl,
$R^2$, $R^4$ and $R^6$ independently of one another represent straight-chain or branched $C_1$-$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, $C_2$-$C_8$-alkenyl, in particular vinyl, allyl, $C_3$-$C_7$-cycloalkyl-$C_1$-$C_4$-alkyl, in particular cyclohexylmethyl, phenyl-$C_1$-$C_4$-alkyl, in particular phenylmethyl which can optionally be substituted by one or more identical or different radicals from amongst those stated above,
and their optical isomers and racemates.

All compounds of the general formula (I) which can exist in optically active, stereoisomeric forms or as racemic mixtures can be used for the purposes of the present invention. However, it is preferred in accordance with the invention to use the optically active, stereoisomeric forms of the compounds of the general formula (I).

The following compounds of the general formula (I) in which
the radicals $R^1$ to $R^6$ have the meanings stated hereinbelow may be mentioned individually:

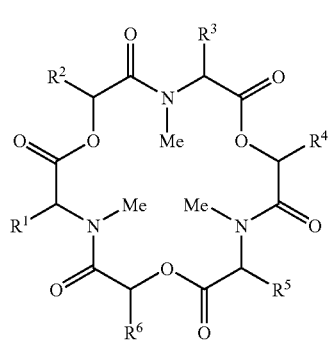

(I)

| $R^1$ | $R^2$ | $R^3$ | $R^4$ | $R^5$ | $R^6$ |
|---|---|---|---|---|---|
| —CHMeCH$_2$Me | -cyclohexyl | —CHMeCH$_2$Me | —Me | —CHMeCH$_2$Me | —Me |
| —CHMeCH$_2$Me | -cyclohexyl | —CHMeCH$_2$Me | —Me | —CHMeCH$_2$Me | -cyclohexyl |
| —CHMeCH$_2$Me | —CH$_2$—Phe | —CHMeCH$_2$Me | —Me | —CHMeCH$_2$Me | —Me |
| —CHMeCH$_2$Me | —CH$_2$—Phe | —CHMeCH$_2$Me | —Me | —CHMeCH$_2$Me | —CH$_2$—Phe |
| —CHMeCH$_2$Me | —(CH$_2$)$_3$—Me | —CHMeCH$_2$Me | —Me | —CHMeCH$_2$Me | —Me |
| —CHMeCH$_2$Me | —(CH$_2$)$_3$—Me | —CHMeCH$_2$Me | —Me | —CHMeCH$_2$Me | —(CH$_2$)$_3$—Me |
| —CHMe$_2$ | —CH$_2$—Phe | —CHMeCH$_2$Me | —Me | —CHMeCH$_2$Me | —Me |
| —CH$_2$—Phe | —CHMe$_2$ | —CH$_2$—Phe | —CHMe$_2$ | —CHMeCH$_2$Me | —CHMe$_2$ |
| —CH$_2$CHMe$_2$ | —CH$_2$—Phe | —CH$_2$CHMe$_2$ | —Me | —CH$_2$CHMe$_2$ | —CH$_2$—Phe |
| —(CH$_2$)$_3$—Me | —Me | —CHMeCH$_2$Me | —Me | —CHMeCH$_2$Me | —Me |
| —CHMe$_2$ | —Me | —CHMe$_2$ | —Me | —CHMe$_2$ | —Me |
| —CH$_2$—Me | —Me | —CH$_2$—Me | —Me | —CH$_2$—Me | —Me |
| —(CH$_2$)$_2$—Me | —Me | —(CH$_2$)$_2$—Me | —Me | —(CH$_2$)$_2$—Me | —Me |
| —(CH$_2$)$_3$—Me | —Me | —(CH$_2$)$_3$—Me | —Me | —(CH$_2$)$_3$—Me | —Me |
| —CH$_2$—CH=CH$_2$ | —Me | —CH$_2$—CH=CH$_2$ | —Me | —(CH$_2$)$_2$—CH=CH$_2$ | —Me |
| —CHMeCH$_2$Me | —Me | —CHMeCH$_2$Me | —Me | —CHMeCH$_2$Me | —CH$_2$—Me |
| —CHMeCH$_2$Me | —Me | —CHMeCH$_2$Me | —Me | —CHMeCH$_2$Me | —(CH$_2$)$_2$—Me |
| —CHMeCH$_2$Me | —Me | —CHMeCH$_2$Me | —Me | —CHMeCH$_2$Me | —(CH$_2$)$_3$—Me |
| —CHMeCH$_2$Me | —Me | —CHMeCH$_2$Me | —Me | —CH$_2$Me | —Me |
| —CHMeCH$_2$Me | —Me | —CHMeCH$_2$Me | —Me | —(CH$_2$)$_2$—Me | —Me |
| -cyclohexyl | —Me | -cyclohexyl | —Me | -cyclohexyl | —Me |
| —CH$_2$CHMe$_2$ | -cyclohexyl | —CH$_2$CHMe$_2$ | —Me | —CH$_2$CHMe$_2$ | -cyclohexyl |
| —CH$_2$CHMe$_2$ | -cyclohexyl | —CH$_2$CHMe$_2$ | —Me | —CH$_2$CHMe$_2$ | —Me |
| —CHMeCH$_2$Me | —CHMe$_2$ | —CHMeCH$_2$Me | —CHMe$_2$ | —CHMeCH$_2$Me | —Me |
| —CH$_2$—Phe | —Me | —CH$_2$—Phe | —Me | —CH$_2$—Phe | —Me |
| -cyclohexyl | —Me | -cyclohexyl | —Me | -cyclohexyl | —Me |
| —CHMe$_2$ | —CHMe$_2$ | —CHMe | —Me | —CHMe$_2$ | —Me |
| —CHMe$_2$ | —CHMe$_2$ | —CHMe$_2$ | —CHMe$_2$ | —CHMe$_2$ | —Me |
| —CH$_2$—Me | —CHMe$_2$ | —CH$_2$Me | —Me | —CH$_2$—Me | —Me |
| —CH$_2$—Me | —CHMe$_2$ | —CHMe$_2$ | —CHMe$_2$ | —CH$_2$—Me | —Me |
| —(CH$_2$)$_2$—Me | —CHMe$_2$ | —(CH$_2$)$_2$—Me | —Me | —(CH$_2$)$_2$—Me | —Me |
| —(CH$_2$)$_2$—Me | —CHMe$_2$ | —(CH$_2$)$_2$—Me | —CHMe$_2$ | —(CH$_2$)$_2$—Me | —Me |

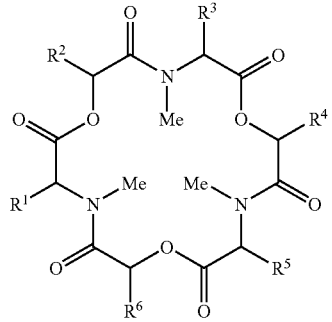

(I)

| R¹ | R² | R³ | R⁴ | R⁵ | R⁶ |
|---|---|---|---|---|---|
| —(CH₂)₃—Me | —CHMe₂ | —(CH₂)₃—Me | —Me | —(CH₂)₃—Me | —Me |
| —(CH₂)₃—Me | —CHMe₂ | —(CH₂)₃—Me | —CHMe₂ | —(CH₂)₃—Me | —Me |
| —CH₂—CH=CH₂ | —CHMe₂ | —CH₂—CH=CH₂ | —Me | —CH₂—CH=CH₂ | —Me |
| —CH₂—CH=CH₂ | —CHMe₂ | —CH₂—CH=CH₂ | —CHMe₂ | —CH₂—CH=CH₂ | —Me |
| —Me | —Me | —CHMeCH₂Me | —Me | —CH₂—Me | —Me |
| —Me | —Me | —CHMeCH₂Me | —Me | —(CH₂)₃—Me | —Me |

Me = methyl;
Phe = phenyl

A further depsipeptide which may be mentioned is the compound PF 1022, which is disclosed in EP-OS 382 173 and has the following formula:

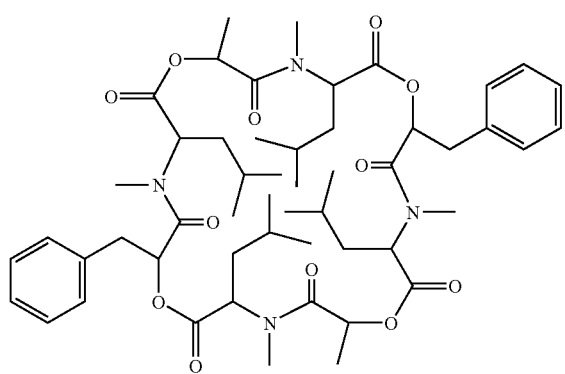

Moreover, depsipeptides which may be mentioned are the compounds disclosed in PCT Application WO 93/19053.

Compounds from PCT Application WO 93/19053 which may be mentioned in particular are those of the following formula:

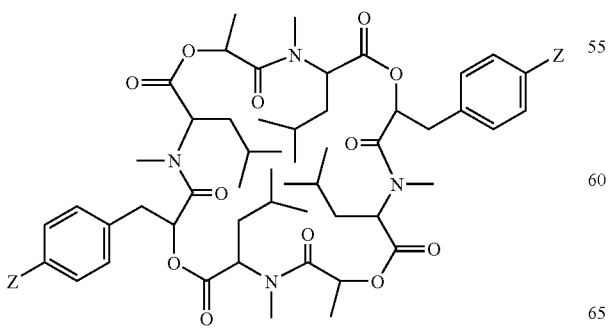

in which z represents N-morpholinyl, amino, mono- or dimethylamino.

An especially preferred example of these compounds is the bis-morpholino derivative cyclo[D-2-hydroxypropanoyl-N-methyl-L-leucyl-3-[4-(4-morpholinyl)phenyl]-D-2-hydroxypropanoyl-N-methyl-L-leucyl-D-2-hydroxypropanoyl-N-methyl-L-leucyl-3[4-(4-morpholinyl)phenyl]-D-2-hydroxypropanoyl-N-methyl-L-leucyl] (CAS 155030-63-0).

Compounds which may additionally be mentioned are those of the following formula:

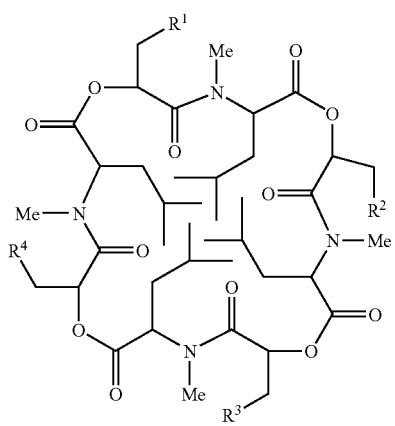

in which $R^1$, $R^2$, $R^3$, $R^4$ independently of one another represent hydrogen, $C_1$-$C_{10}$-alkyl or aryl, in particular phenyl, which are optionally substituted by hydroxyl, $C_1$-$C_{10}$-alkoxy or halogen.

The compounds of the general formula (I) are known and can be obtained by the processes described in EP-A-382 173, DE-A 4 317 432, DE-A 4 317 457, DE-A 4 317458, EP-A-634 408, EP-A-718 293, EP-A-872 481, EP-A-685 469, EP-A-626 375, EP-A-664 297, EP-A-669 343, EP-A-787 141, EP-A-865 498, EP-A-903 347.

The cyclic depsipeptides having 24 ring atoms also include compounds of the general formula (Ia)

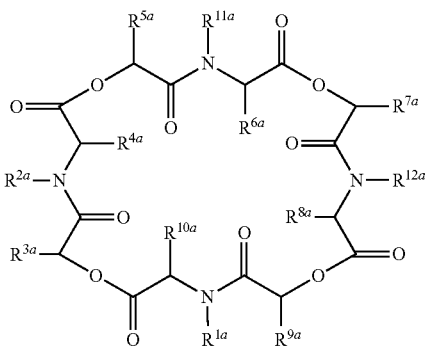

(Ia)

in which
$R^{1a}$, $R^{2a}$, $R^{11a}$ and $R^{12a}$ independently of one another represent $C_{1-8}$-alkyl, $C_{1-8}$-halogenoalkyl, $C_{3-6}$-cycloalkyl, aralkyl, aryl,
$R^{3a}$, $R^{5a}$, $R^{7a}$, $R^{9a}$ independently of one another represent hydrogen or straight-chain or branched $C_{1-8}$-alkyl which can optionally be substituted by hydroxyl,

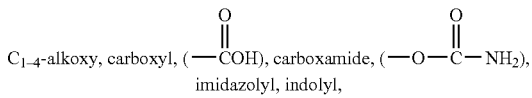

$C_{1-4}$-alkoxy, carboxyl, (—COH), carboxamide, (—O—C—NH$_2$), imidazolyl, indolyl, guanidino, —SH or $C_{1-4}$-alkylthio, and furthermore represent aryl or aralkyl, each of which can be substituted by halogen, hydroxyl, $C_{1-4}$-alkyl, $C_{1-4}$-alkoxy,
$R^{4a}$, $R^{6a}$, $R^{8a}$, $R^{10a}$ independently of one another represent hydrogen, or represent straight-chain $C_{1-5}$-alkyl, $C_{2-6}$-alkenyl, $C_{3-7}$-cycloalkyl, each of which can optionally be substituted by hydroxyl, $C_{1-4}$-alkoxy, carboxyl, carboxamide, imidazolyl, indolyl, guanidino, SH or $C_{1-4}$-alkylthio, and represent aryl or aralkyl, each of which can be substituted by halogen, hydroxyl, $C_{1-4}$-alkyl, $C_{1-4}$-alkoxy,
and their optical isomers and racemates.

Compounds of the formula (Ia) which are preferably employed are those in which
$R^{1a}$, $R^{2a}$, $R^{11a}$ and $R^{12a}$ independently of one another represent methyl, ethyl, propyl, isopropyl, n-, s-, t-butyl or phenyl, which is optionally substituted by halogen, $C_{1-4}$-alkyl, OH, $C_{1-4}$-alkoxy, and represent benzyl or phenylethyl, each of which can optionally be substituted by the radicals stated for phenyl;
$R^{3a}$ to $R^{10a}$ have the abovementioned meaning.

Especially preferred compounds of the formula (Ia) are those in which
$R^{1a}$, $R^{2a}$, $R^{11a}$ and $R^{12a}$ independently of one another represent methyl, ethyl, propyl, isopropyl or n-, s-, t-butyl,
$R^{3a}$, $R^{5a}$, $R^{7a}$, $R^{9a}$ represent hydrogen, or represent straight-chain or branched $C_{1-8}$-alkyl, in particular methyl, ethyl, propyl, i-propyl, n-, s-, t-butyl, each of which can optionally be substituted by $C_{1-4}$-alkoxy, in particular methoxy, ethoxy, imidazolyl, indolyl or $C_{1-4}$-alkylthio, in particular methylthio, ethylthio, furthermore represent phenyl, benzyl or phenethyl, each of which can optionally be substituted by halogen, in particular chlorine, $R^{4a}$, $R^{6a}$, $R^{8a}$, $R^{10a}$ independently of one another represent hydrogen, or represent methyl, ethyl, n-propyl, n-butyl, vinyl, cyclohexyl, each of which can optionally be substituted by methoxy, ethoxy, imidazolyl, indolyl, methylthio, ethylthio, and represent isopropyl, s-butyl, and furthermore in each case optionally halogen-substituted phenyl, benzyl or phenylethyl.

The compounds of the formula (Ia) can also be obtained by the processes described in EP-A-382 173, DE-A 4 317 432, DE-A 4 317 457, DE-A 4 317 458, EP-A-634 408, EP-A-718 293, EP-A-872 481, EP-A-685 469, EP-A-626 375, EP-A-664 297, EP-A-669 343, EP-A-787 141, EP-A-865 498, EP-A-903 347.

The compositions according to the invention are suitable for controlling pathogenic endoparasites found in humans and in animal keeping and livestock breeding in productive livestock, breeding animals, zoo animals, laboratory animals, experimental animals and pets while having favourable toxicity to warm-blooded species. They are active against all or individual developmental stages of the pests and against resistant and normally sensitive species. By controlling the pathogenic endoparasites, it is intended to reduce disease, death and reduced performance (for example in the production of meat, milk, wool, hides, eggs, honey and the like), so that more economical and simpler animal keeping is possible by using the active compounds. The pathogenic endoparasites include cestodes, trematodes, nematodes, acantocephala, in particular:

From the order of the Pseudophyllidea, for example: *Diphyllobothrium* spp., *Spirometra* spp., *Schistocephalus* spp., *Ligula* spp., *Bothridium* spp., *Diphlogonoporus* spp.

From the order of the Cyclophyllidea, for example: *Mesocestoides* spp., *Anoplocephala* spp., *Paranoplocephala* spp., *Moniezia* spp., *Thysanosomsa* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

From the sub-class of the Monogenea, for example: *Gyrodactylus* spp., *Dactylogyrus* spp., *Polystoma* spp.

From the sub-class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp-, *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp. *Metorchis* spp., *Heterophyes* spp., *Metagonimus* spp.

From the order of the Enoplida, for example: *Trichuris* spp., *Capillaria* spp., *Trichomosoides* spp., *Trichinella* spp.

From the order of the Rhabditia, for example: *Micronema* spp., *Strongyloides* spp.

From the order of the Strongylida, for example: *Stronylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp.,

*Globocephalus* spp., *Syngamus* spp., *Cyathostoma* spp., *Metastrongylus* spp., *Dictyocaulus* spp., *Muellerius* spp., *protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

From the order of the Oxyurida, for example: *Oxyuris* spp., *Enterobius* spp., *Passalurus* spp., *Syphacia* spp., *Aspiculuris* spp., *Heterakis* spp.

From the order of the Ascaridia, for example: *Ascaris* spp., *Toxascaris* spp., *Toxocara* spp., *Parascaris* spp., *Anisakis* spp., *Ascaridia* spp.

From the order of the Spirurida, for example: *Gnathostoma* spp., *Physaloptera* spp., *Thelazia* spp., *Gongylonema* spp., *Habronema* spp., *Parabronema* spp., *Draschia* spp., *Dracunculus* spp.

From the order of the Filariida, for example: *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

From the order of the Gigantorhynchida, for example: *Filicollis* spp., *Moniliformis* spp., *Macracanthorhynchus* spp., *Prosthenorchis* spp.

Other productive livestock are breeding animals including mammals such as, for example, cattle, horses, sheep, pigs, goats, camels, water buffaloes, donkeys, rabbits, fallow deer, reindeer, fur bearers such as, for example, mink, chinchilla and racoon, birds such as, for example, chickens, geese, turkeys, ducks and ostriches, fresh water and salt water fish such as, for example, trout, salmon, carp and eels, reptiles, and insects such as, for example, honeybee and silkworm.

Laboratory animals and experimental animals include mice, rats, guinea pigs, golden hamsters, dogs and cats.

The pets include dogs and cats.

The compositions according to the invention are particularly preferably employed in dogs and cats, in particular dogs.

Application can be effected both prophylactically and therapeutically.

The shaped articles according to the invention can also be used as carriers for the administration of other active compounds. Examples which may be mentioned are: other active compounds which act against pathogenic endoparasites such as, for example, L-2,3,5,6-tetrahydro-6-phenylimidazothiazole, benzimidazolecarbamates such as febantel, furthermore pyrantel, praziquantel and ivermectin; coccidiostats such as toltrazuril and ponazuril (=toltrazuril-sulphone); painkillers such as flupirtin and antibiotics such as enrofloxacin, and the compounds described in WO 97/31001, in particular 8-cyano-1-cyclopropyl-7-((1S,6S)-2,8-diazabicyclo[4.3.0] nonan-8-yl)-6-fluoro-1,4-dihydro-4-oxo-3-quinolinecarboxylic acid of the formula

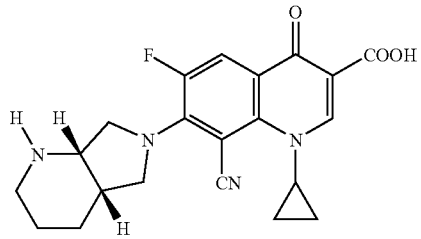

In the shaped articles according to the invention, the active compounds can also be employed in combination with synergists or with other suitable active compounds. For example, the depsipeptides stated further above can be combined with other active compounds against pathogenic endoparasites, for example those which have been mentioned further above.

Ready-for-use preparations comprise the active compounds in concentrations from 10 ppm-25 percent by weight, preferably 0.1-20 percent by weight.

To achieve effective results, it has generally proved advantageous to administer amounts of the mixture according to the invention of approximately 0.001 to approximately 100 mg of active compound per kg of bodyweight per day. Preferred are 0.005 to 5 mg of active compound per kg of bodyweight.

Ancillairy substances which are used are: starch such as, for example, starch from wheat, rice, maize, tapioca, rye, oats and potatoes. Modified starches can be physically pretreated starches such as pregelatinized or chemically modified starches such as hydroxyethylstarch, hydroxypropylstarch, methylstarch, carboxymethylstarch, starch acetate, hydroxypropylstarch acetate, hydroxyethylstarch acetate, starch phosphates, starch sulphates, or chemically or ionically crosslinked starches such as dye-starch phosphates, phosphates of hydroxypropylated starches, starch dicarboxylic acid diesters or salts of anionic starch derivatives. Preferred are hydroxypropylated and phosphate-crosslinked starches of maize, wheat, tapioca and potato. Starch quantities of between 30% and 80%, preferably between 40% and 70%, especially preferably between 40 and 60%, are employed in this context. The percentages are percent by weight of the finished composition.

Sugars such as sucrose, glucose, fructose, mannose and sorbitol are furthermore used. Quantities of between 1% and 20%, preferably between 1% and 15%, especially preferably between 1% and 10%, are employed in this context. The percentages are percent by weight of the finished composition.

Materials which are especially suitable for shaping and bodying are cellulose and its derivatives such as microcrystalline cellulose, hydroxypropylcellulose, methylhydroxypropylcellulose, carboxymethylcellulose, especially cellulose acetate and very especially cellulose-2,5-acetate. Materials which are furthermore suitable are highly-dispersed silicates and titanium dioxide. Amounts of between 1% and 40%, preferably between 1% and 30%, especially preferably between 1 and 20%, are employed in this context. The percentages are percent by weight of the finished composition.

Materials which act as humectants and plasticizers are water, glycerol, propylene glycol, polyethylene glycols and polypropylene glycols. Amounts of between 1% and 30%, preferably between 5% and 30%, especially preferably between 5 and 20%, are employed in this context. The percentages are percent by weight of the finished composition.

Preservatives which can be employed are compounds conventionally used for pharmaceutical preparations and foodstuffs, such as benzoic esters, methyl p-hydroxybenzoate, ethyl p-hydroxybenzoate, propyl p-hydroxybenzoate, sorbic acid, propyl gallate, citric acid, ascorbic acid, ascorbin palmitate, tocopherol, tocopherol acetate, butylhydroxytoluene and butylhydroxyanisole.

Emulsifiers which can be employed are: surfactants such as
1. nonionic surfactants, for example polyoxyethylated castor oil, polyoxyethylated sorbitan monooleate, sorbitan monostearate, ethyl alcohol, glycerol monostearate, polyoxyethyl stearate, alkylphenol polylglycol ethers,
2. ampholytic surfactants, such as disodium N-lauryl-B-iminodipropionate or lecithin,
3. anionic surfactants, such as sodium lauryl sulphate, fatty alcohol ether sulphates, mono/dialkyl polyglycol ether orthophosphoric ester monoethanolamine salt.

The quantities employed here preferably amount to 0.05% by weight to 2% by weight, based on the total amount of constituents. Quantities of from 0.2 to 1% by weight are especially preferred.

Ideally, the shaped articles according to the invention have a Shore A hardness of 10 to 100, preferably 10 to 65, very especially preferably 10 to 30, in particular 15 to 25. The Shore A hardness is determined as specified by DIN Method 53505.

Suitable aromas are powdered liver from cattle, poultry, sheep or pigs, preferably poultry and pigs, and other aroma preparations. Amounts of between 1% and 30%, preferably between 5% and 25%, especially preferably between 5% and 20%, are employed in this context. The percentages are percent by weight of the finished composition.

Very especially suitable are the aromas which are commerically available from Pharmachem (BEEF®) and Haarmann und Reimer (BAYOPAL®) under the names BEEF® and BAYOPAL®.

The examples which follow illustrate the invention without imposing any limitation. The active compound employed in the examples is the compound cyclo[D-2-hydroxypropanoyl-N-methyl-L-leucyl-3-[4-(4-morpholinyl)phenyl]-D-2-hydroxypropanoyl-N-methyl-L-leucyl-D-2-hydroxypropanoyl-N-methyl-L-leucyl-3 [4-(4-morpholinyl)phenyl]-D-2-hydroxypropanoyl-N-methyl-L-leucyl] (CAS 155030-63-0).

BRIEF DESCRIPTION OF THE DRAWING

The FIGURE shows the acceptance of the placebo and the verum samples as detailed in Example 3.

EXAMPLE 1

55% of wheat flour, 10% of fructose, 10% of beef aroma, Pharma-Chemie, 1% of Aerosil and 4% of depsipeptide are homogenized and screened and the mixture is subsequently fed to an extruder via a measuring screw. Accordingly, 5% of water and 15% of glycerol (based on the total mixture) are pumped in via a metering pump. The extrusion temperature is 120° C. The extrudate formed is cut into pieces so that one piece contains the dose for 10 kg of the animal's bodyweight. The percentages here are to be understood as percent by weight.

EXAMPLE 2

45% of cornstarch, 10% of sucrose, 10% of liver aroma, Haarmann & Reimer, 10% of cellulose acetate powder, 1% of Aerosil and 4% of depsipeptide are homogenized and screened and the mixture is subsequently fed to an extruder via a measuring screw. Accordingly, 5% of water and 15% of glycerol (based on the total mixture) are pumped in via a metering pump. The extrusion temperature is 120° C. The extrudate formed is cut into pieces so that one piece contains the dose for 10 kg of the animal's bodyweight. The percentages here are to be understood as percent by weight.

EXAMPLE 3

The samples prepared in Example 2 are fed to dogs. Both placebo sample (without active compound) and verum sample (with active compound) are tested against a commercially available food which contains meat ("Frolic"). The acceptance of the placebo and the verum samples is comparable as shown in the FIGURE.

EXAMPLE 4

The samples of Example 1 or 2 are fed to parasite-infected dogs at a dosage of 5 mg of depsipeptide per kg of bodyweight. After two to four days, the animals are free of parasites.

| Animal | Parasite | Effect |
| --- | --- | --- |
| 2 dogs | *Toxocara canis* | 3/3 |
| 2 dogs | *Ancylostoma caninum* | 3/3 |

The invention claimed is:

1. A starched-based extruded shaped article which has a Shore A hardness of 10 to 100, characterized in that the article comprises a combination of one or more specific aromas, one or more bodying agents and one or more pharmaceutically active compounds for animals.

2. Starch-based extruded shaped articles according to claim 1, wherein the aroma is selected from the group consisting of poultry liver aroma and meat aroma.

3. Starch-based extruded shaped articles according to claim 1, wherein the pharmaceutically active compound is a cyclic depsipeptides composed of amino acids and hydrocarboxylic acids as units and having 6 to 30 ring or chain atoms.

4. Starch-based extruded shaped articles according to claim 1, further comprising pulverulent cellulose acetate.

5. Starch-based extruded shaped articles according to claim 1, further comprising ancillary materials selected from the group consisting of emulsifiers, humectants and preservatives.

6. Process for the preparation of starch-based extruded shaped articles according to claim 1, wherein the aroma, bodying agent, and pharmaceutically active compound are mixed and processed at extrusion temperatures of less than 150° C.

7. Starch-based extruded shaped articles according to claim 2, wherein the pharmaceutically active compound is a cyclic depsipeptides composed of amino acids and hydroxycarboxylic acids as units and having 6 to 30 ring or chain atoms.

8. Starch-based extruded shaped articles according to claim 2, further comprising pulverulent cellulose acetate.

9. Starch-based extruded shaped articles according to claim 2, further comprising ancillary materials selected from the group consisting of emulsifier, humectants, and preservatives.

10. Starch-based extruded shaped articles according to claim 3, further comprising ancillary materials selected from the group consisting of emulsifiers, humectants, and preservatives.

11. Process for the preparation of starch-based extruded shaped articles according to claim 2, wherein the aroma, bodying agent, and pharmaceutically active compound are mixed and processed at extrusion temperatures of less than 150° C.

12. Process for the preparation of starch-based extruded shaped articles according to claim 3, wherein the aroma, bodying agent, and pharmaceutically active compound are mixed and processed at extrusion temperatures of less than 150° C.

13. A starched-based extruded shaped article, characterized in that the article comprises a combination of one or more specific aromas, one or more bodying agents and one or more cyclic depsipeptide composed of amino acids and hydrocarboxylic acids as units and having 6 to 30 ring or chain atoms and wherein the shaped article has a Shore A hardness of 10 to 65.

14. A starched-based extruded shaped article which has a Shore A hardness of 10 to 100, characterized in that the article comprises a combination of one or more specific aromas, one or more bodying agents and one or more cyclic depsipeptide composed of amino acids and hydrocarboxylic acids as units and having 6 to 30 ring or chain atoms, wherein the aroma, bodying agent, and cyclic depsipeptide are mixed and processed at extrusion temperatures of less than 150° C.

* * * * *